US009205216B2

(12) United States Patent
O'Leary

(10) Patent No.: US 9,205,216 B2
(45) Date of Patent: Dec. 8, 2015

(54) APPARATUS FOR POSITIONING A NASAL CANNULA

(75) Inventor: John P. O'Leary, Fort Collins, CO (US)

(73) Assignee: 0200L, LLC, Fort Collins, CO (US)

( * ) Notice: Subject to any disclaimer, the term of this patent is extended or adjusted under 35 U.S.C. 154(b) by 609 days.

(21) Appl. No.: 13/329,198

(22) Filed: Dec. 16, 2011

(65) Prior Publication Data

US 2012/0167894 A1     Jul. 5, 2012

Related U.S. Application Data

(60) Provisional application No. 61/428,933, filed on Dec. 31, 2010.

(51) Int. Cl.
*A61M 16/06* (2006.01)
*A61M 25/02* (2006.01)

(52) U.S. Cl.
CPC ....... *A61M 16/0683* (2013.01); *A61M 16/0666* (2013.01); *A61M 2025/0226* (2013.01); *A61M 2210/0618* (2013.01); *A61M 2210/0625* (2013.01)

(58) Field of Classification Search
CPC ..................... A61M 16/0666; A61M 16/0683; A61M 25/02; A61M 16/0488; A61M 16/0672; A61M 2025/0226; Y10S 128/26
USPC .............. 128/200.24, 200.26, 207.18, 206.11
See application file for complete search history.

(56) References Cited

U.S. PATENT DOCUMENTS

| | | | |
|---|---|---|---|
| 3,513,844 A * | 5/1970 | Smith | 128/207.18 |
| 4,222,378 A * | 9/1980 | Mahoney | 128/206.24 |
| 4,367,735 A | 1/1983 | Dali | |
| 5,135,506 A * | 8/1992 | Gentelia et al. | 604/180 |
| 5,335,656 A * | 8/1994 | Bowe et al. | 128/207.18 |
| 5,513,635 A | 5/1996 | Bedi | |
| 5,533,506 A * | 7/1996 | Wood | 128/207.18 |
| 5,682,881 A * | 11/1997 | Winthrop et al. | 128/207.18 |
| 6,279,577 B1 | 8/2001 | Savaiano | |
| 6,763,832 B1 | 7/2004 | Kirsch et al. | |
| 6,986,353 B2 | 1/2006 | Wright | |
| 7,007,694 B2 | 3/2006 | Aylsworth et al. | |
| 8,096,300 B2 * | 1/2012 | Russo | 128/207.17 |
| 2001/0032645 A1 * | 10/2001 | Cronk et al. | 128/200.24 |

(Continued)

OTHER PUBLICATIONS

International Search Report for PCT/US10/24152, International Searching Authority, Apr. 26, 2010, pp. 1-8.

(Continued)

*Primary Examiner* — Lynne Anderson
*Assistant Examiner* — Bradley Philips
(74) *Attorney, Agent, or Firm* — Samuel M. Freund; Cochran Freund & Young LLC

(57) ABSTRACT

An apparatus and a system for stably positioning a nasal cannula in a manner effective for oral or nasal delivery of oxygen or gas mixtures to an individual are described. A generally rectangular cannula support member having at least one retention device secures a nasal cannula to the support member. A pad may be disposed between the support member and the face of the person to assist in positioning the support member without the requirement of tape, and for reducing skin irritation. Depending on the size of the cannula support member, the support member may be constructed from flexible materials to conform to the facial features of the wearer. The apparatus and the system may further include a flexible strip having shape memory.

26 Claims, 5 Drawing Sheets

(56) References Cited

U.S. PATENT DOCUMENTS

| | | |
|---|---|---|
| 2003/0056785 A1 | 3/2003 | Narihiko et al. |
| 2004/0187873 A1 | 9/2004 | Brown |
| 2005/0066976 A1 | 3/2005 | Wondka |
| 2007/0095347 A1 | 5/2007 | Lampotang et al. |
| 2008/0078414 A1 | 4/2008 | Demas |
| 2008/0190436 A1* | 8/2008 | Jaffe et al. ............... 128/207.18 |
| 2008/0216838 A1* | 9/2008 | Wondka .................. 128/205.25 |
| 2010/0000534 A1 | 1/2010 | Kooij et al. |
| 2010/0206312 A1* | 8/2010 | O'Leary ................. 128/207.18 |
| 2011/0197689 A1 | 8/2011 | Haveri et al. |
| 2013/0008449 A1* | 1/2013 | Busch et al. ............. 128/206.21 |

OTHER PUBLICATIONS

International Search Report, International Searching Authority, Apr. 3, 2012, pp. 1-15.

\* cited by examiner

APPARATUS FOR POSITIONING A NASAL CANNULA

CROSS-REFERENCE TO RELATED APPLICATIONS

The present application claims the benefit of U.S. Provisional Patent Application No. 61/428,933 for "APPARATUS FOR POSITIONING A NASAL CANNULA" by John P. O'Leary, which was filed on Dec. 31, 2010, the entire content of which is hereby specifically incorporated by reference herein for all that it discloses and teaches.

FIELD OF THE INVENTION

The present invention relates generally to nasal cannulas and, more particularly, to an apparatus for positioning a nasal cannula such that gas may be orally or nasally administered to a person.

BACKGROUND OF THE INVENTION

Nasal cannulas are well-known devices for delivering low flows (1-6 l/min.) of supplemental or therapeutic oxygen to persons needing additional oxygen, where detailed control of respiration rate is not required. Such devices find significant use in elderly patients who need oxygen therapy. Typically, nasal cannulas include a hollow body portion having a pair of spaced-apart, curved elongated tubular portions (nasal interface or nasal prongs) extending through a surface of the body and in fluid communication with the hollow volume thereof. The tubular portions through which oxygen is caused to flow are adapted to fit into the nares of a person. Two flexible plastic tubes in fluid contact with a source of oxygen are attached to the body, one at each end thereof, are disposed behind the ears of a person and brought into mechanical contact under the chin of the person by means of a loop adjustment collar or slide, as an example. Cannulas may be single lumen in which situation a single flow path exists between the patient and a source of oxygen, that is, the plastic tubes may merge into a single tube by means of a tee under the chin, as an example, or dual lumen where the flow paths to each naris may be separated by a barrier or bifurcation, and the two plastic tubes are supplied using different oxygen sources or gas regulators, as examples.

Oro-nasal cannulas are also known, although uncommon, wherein a third plastic tube is run parallel to one of the nasal supply tubes and mechanically coupled thereto. The third tube may be connected to a second or third oxygen source or gas regulator, depending upon the design of the nasal portion of the cannula. Through insertion of the tubular extensions into the nares, looping the oxygen supply tubes over the ears and combining the tubes under the chin, as an example, a nasal or oral-nasal cannula may be firmly affixed to a person, wherein it remains in place during periods of sleep or walking, as examples.

Patients undergoing continuous oximetry monitoring (measurement of oxygen saturation of the blood by means of an oximeter) often display desaturation while sleeping. Plethysmographic assessment of the individual generally uncovers no change in the air volume flowing, and the patient must be awakened and encouraged to breathe through the nose, wherein oxygen saturation improves. As the patient returns to sleep, the cannula remains in the nose, and desaturation returns. Thus, nasal cannulas positioned in the nares are ineffective for delivery of oxygen to mouth breathers. Further, breathing impairment conditions such as nasal/sinus congestion, nose bleeds, deviated septum, and nose injury, all prevent proper oxygen saturation using a nasal cannula positioned in the nares. An Oximizer® oxygen-conserving nasal cannula may be useful for better oxygen delivery at higher oxygen flow levels, but the difficulty remains for mouth breathing individuals and those with breathing impairments.

Oral oxygen delivery using masks (simple masks, face tents, and non-rebreather, venturi and BiPAP (Bi-level Positive Airway Pressure) masks, as examples) are an option. However, $CO_2$ retention, claustrophobia, drying of mucus membranes, communication difficulties, expense and considerable oxygen use make such options less attractive. High oxygen use is generally a problem with oro-nasal cannulas since the oxygen flow may ineffectively continue through the nasal portion of the cannula.

SUMMARY OF THE INVENTION

Accordingly, it is an object of embodiments of the present invention to provide a device for positioning a nasal cannula for orally administering a gas to a person.

Another object of the invention is to provide a device for positioning a nasal cannula for orally administering a gas to a person while minimizing adverse effects to the skin surrounding the mouth.

Yet another object the invention is to provide a device for positioning a nasal cannula for nasally administering a gas to a person.

Still another object of the invention is to provide a device for positioning a nasal cannula for nasally administering a gas to a person while reducing adverse effects to the skin surrounding the nose.

Another object of the invention is to provide a device for positioning a nasal cannula to either nasally or orally administer a gas to a person.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus for positioning a nasal cannula on the face of a person for oral or nasal administration of gas, hereof, includes: a cannula support member having a first end and an opposing second end; at least one retention device for securing the nasal cannula to the support member; and a pad disposed between the support member and the face of the person; whereby, the cannula is held at a chosen location on the face of the person.

In another aspect of the present invention and in accordance with its objects and purposes, the system for oral or nasal administration of gas to a person, hereof, includes: a nasal cannula; a cannula support member having a first end and an opposing second end; at least one retention device for securing the nasal cannula to the support member; and a pad disposed between the support member and the face of the person; whereby, the cannula is held at a chosen location on the face of the person.

Benefits and advantages of embodiments of the present invention include, but are not limited to, providing a device for securely positioning a cannula for orally or nasally delivering gas to a person while overcoming the difficulty of stably maintaining the cannula in contact with bare skin, without the use of tape, and further avoiding the adverse effects of plastic cannulae in long-term contact with bare skin.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE INVENTION

Figure 1:
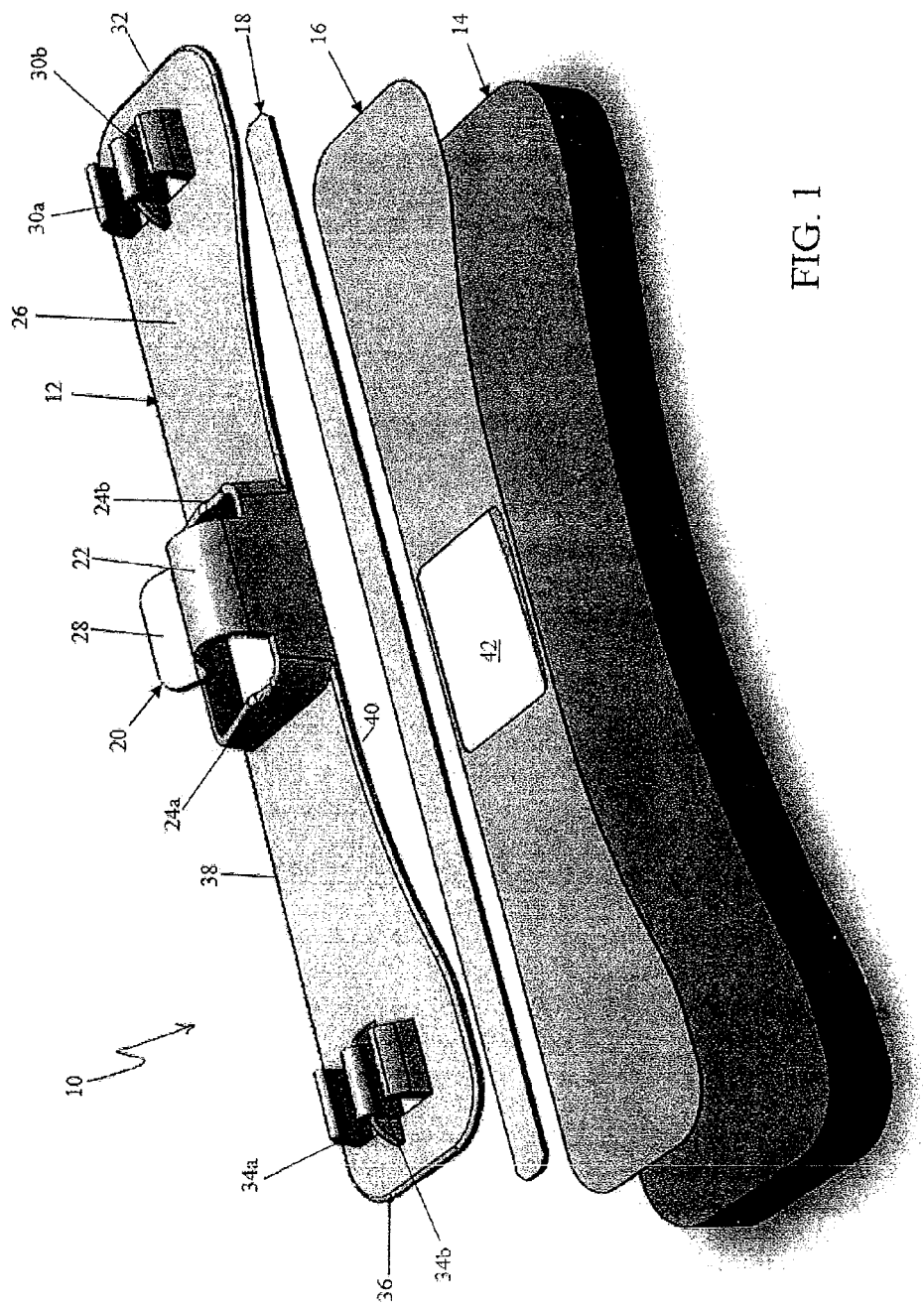
FIG. 1 is a schematic representation of an exploded top perspective view of an embodiment of the apparatus for positioning a nasal cannula, showing the cannula support, a flexible strip, a double-sided adhesive strip and a cloth cushion thereof.

Briefly, embodiments of the present invention include a device for positioning a nasal cannula in a manner effective for oral or nasal delivery of oxygen to an individual. A generally rectangular cannula support member, at least one spring clip or other retention device for securing the nasal cannula to the support member, and at least one raised channel in the vicinity of each end of the support member for securing each of the flexible gas supply tubes on at least one location to the support member, such that a length of each flexible tube forms a loop effective for encircling one ear of the person. A pad may be disposed between the support member and the face of the person to assist in positioning the support member without the requirement of an adhesive tape, and for reducing skin irritation. Depending on the size of the support member, it may be constructed from flexible materials to conform to the facial features of the wearer. To assist in conforming to facial features, the apparatus may further include a flexible strip having shape memory.

Mixtures of gases may also be administered using embodiments of the present invention. Once placed on a person, the apparatus positions the nasal cannula below the lower lip, such that the nasal prongs are disposed facing toward the mouth opening, and may deliver oxygen to a mouth-breathing individual. By placing the cannula support on the upper lip of the individual, such that the nasal prongs are inserted into the nostrils, oxygen may be delivered into the nose. The device overcomes the difficulty of stably positioning a cannula on a bare chin or lip without the use of tape, and the fact that the contour of the lower lip to the chin is oppositely shaped from the curvature of the cannula.

In what follows, the terms "device" and "apparatus" will be used interchangeably, and an embodiment of the term "cannula" includes a device having a central portion comprising an open-ended plastic tube having two open, hollow, parallel tips or prongs disposed perpendicular to the axis of the tubing and adapted for insertion into the front portion of a person's nostrils; and two lengths of open-ended flexible tubing each of which is in gaseous communication with one of the open ends of the tubular central portion, and a source of gas. Another embodiment of a cannula includes a hollow body portion with a pair of parallel spaced-apart, curved elongated tubular portions extending through a surface of the body and in gaseous communication with the hollow volume thereof and adapted for insertion into the front portion of a person's nostrils, and a first and a second length of flexible, open-ended tubing each of which is in gaseous communication with the volume of the body portion and a source of gas. The term "system" includes the combination of embodiments of the present invention with a nasal cannula, and the term "gas" or "gases" includes oxygen, mixtures of gases, and oxygen mixed with other gases. The term "retention device" as used herein includes clamps, clasps, clips, snaps, and the like, and adhesives, for securing the cannula to the cannula holder.

Reference will now be made in detail to the present embodiments of the invention, examples of which are illustrated in the accompanying drawings. In the FIGURES, similar structure will be identified using identical reference characters. Turning now to FIG. 1, shown is a schematic representation of an exploded top perspective view of an embodiment of apparatus, 10, for positioning a nasal cannula, illustrating cannula support, 12, cloth cushion or pad, 14, double-sided adhesive strip, 16, and flexible strip, 18. At least one retention device, 20, having cylindrical portion, 22, and circular notches, 24a, and 24b, attached to top surface, 26, of generally rectangular cannula support 12, is adapted to provide an interference fit over the open-ended plastic tube central portion of a cannula, with cylindrical portion 22 being adapted to fit between the two parallel tips or prongs of the tube. Retention device 20 may further include extension portion, 28, for assisting the introduction and removal of a cannula under cylindrical portion 22 thereof. Retention device 20 may be cemented to cannula support 12, or may be integrally molded therewith. Clearly, other types of retention devices may provide similar functions Interference-fit retainers, 30a, and 30b, emerging from surface 26 near one end, 32, of cannula support 12, and interference-fit retainers, 34a, and 34b, near second, opposing end, 36, of cannula support 12, are provided and adapted for affixing each of the two lengths of open-ended flexible tubing attached to the open ends of the tubular central portion to cannula support 12, respectively, at one or two locations along the tubing, as will be illustrated in FIGS. 4 and 5, hereinbelow. In other embodiments of cannula support 12, a single interference-fit retainer is provided near each end, or no interference fit retainers are provided and the two lengths of open-ended plastic tubing are looped directly around a person's ears, one tube around each ear.

For longer cannula supports 12, the cannula support may be made from flexible materials, such as plastic, and the generally rectangular shape thereof may be made slightly concave on opposing long surfaces, 38, and 40, to more effectively fit the face of a user.

Pad 14 may be fabricated from hypoallergenic materials and adapted to fit between cannula support 12 and the face of a person. Cloth and foam are advantageous in protecting the face of a cannula user from irritation resulting from long-term cannula use. For longer cannula supports, 12, the cannula support may be affixed to pad 14. Double-sided, pressure-sensitive adhesive strip 16 may be used for this purpose. Open portion, 42, beneath retention device 20 enables the cannula to be adjusted on and removed from cannula support 12 since the cannula will not be exposed to adhesive materials. Flexible strip 18, may be fabricated from metal or plastic, or other material having shape memory, and is used in cooperation with pad 14 and adhesive strip 16 to maintain the shape of cannula support 12 once it is adjusted to the face of an individual. Aluminum is an exemplary material for this purpose.

Figure 2:
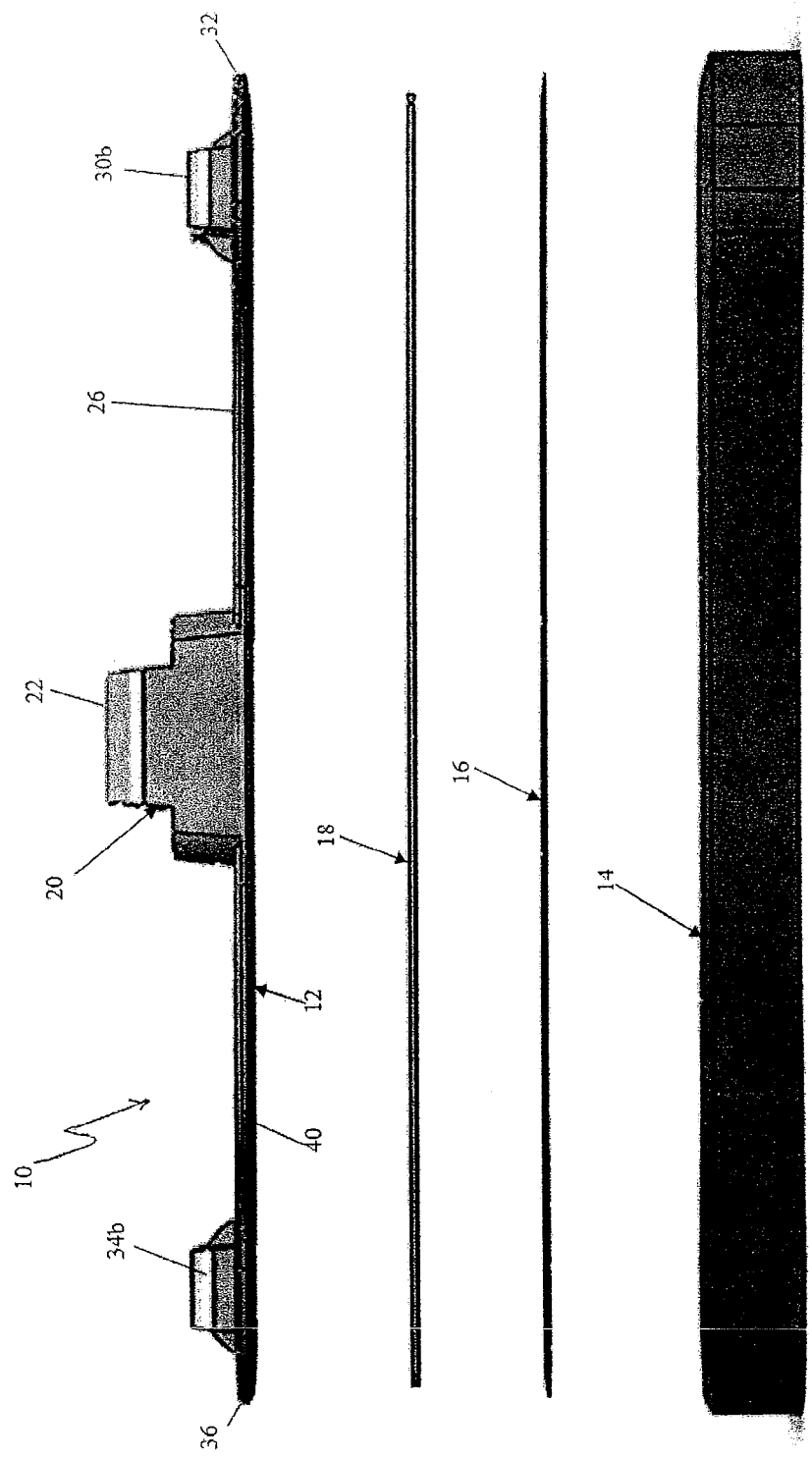
FIG. 2 is a schematic representation of an exploded side view of the embodiment of the invention shown in FIG. 1 hereof.

FIG. 2 is a schematic representation of an exploded side view of the embodiment of the invention shown in FIG. 1 hereof.

Figure 3:
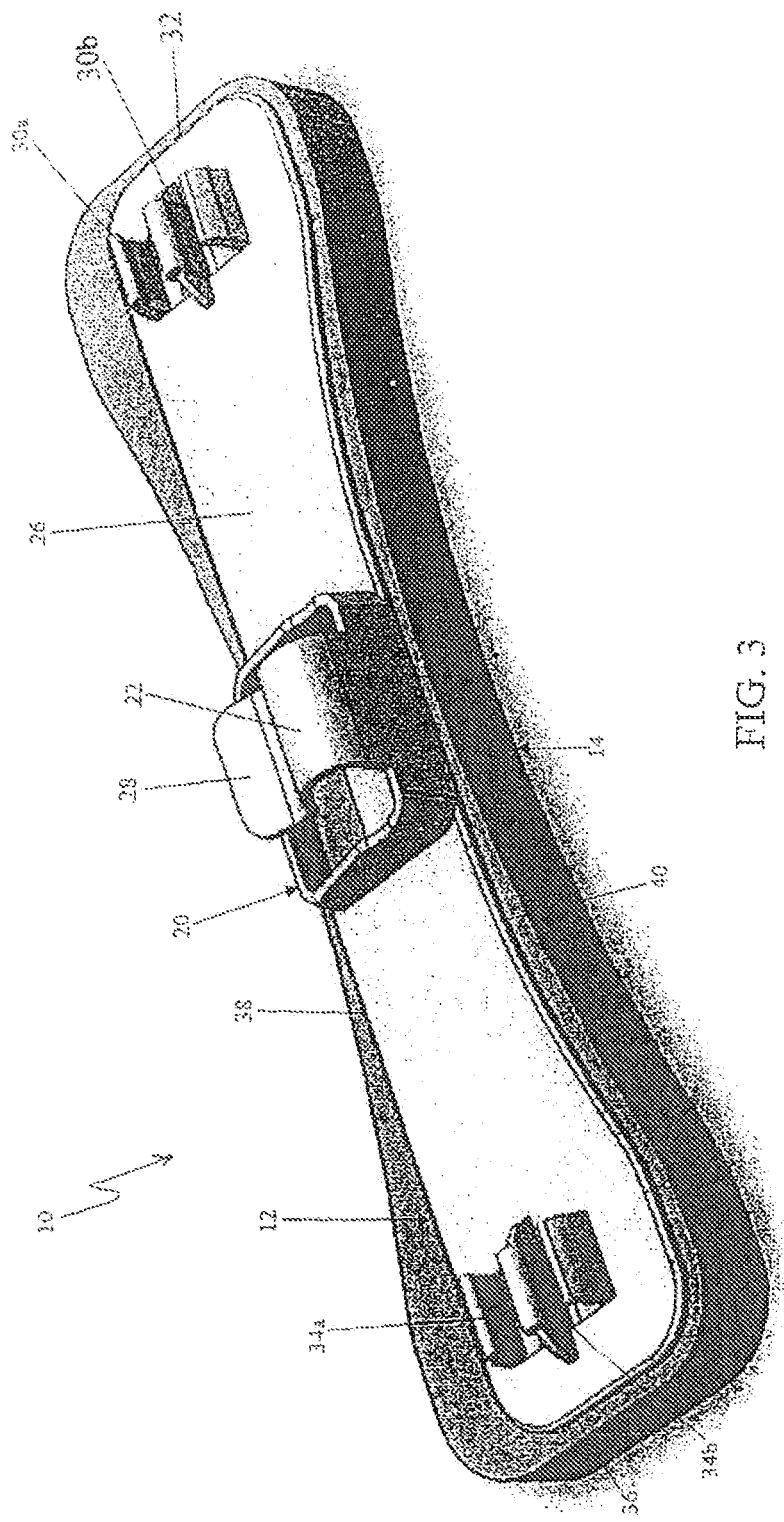
FIG. 3 is a schematic representation of a top perspective view of the assembled embodiment shown in FIG. 1 hereof.

FIG. 3 is a schematic representation of a top perspective view of the assembled embodiment shown in FIG. 1 hereof.

Figure 4:
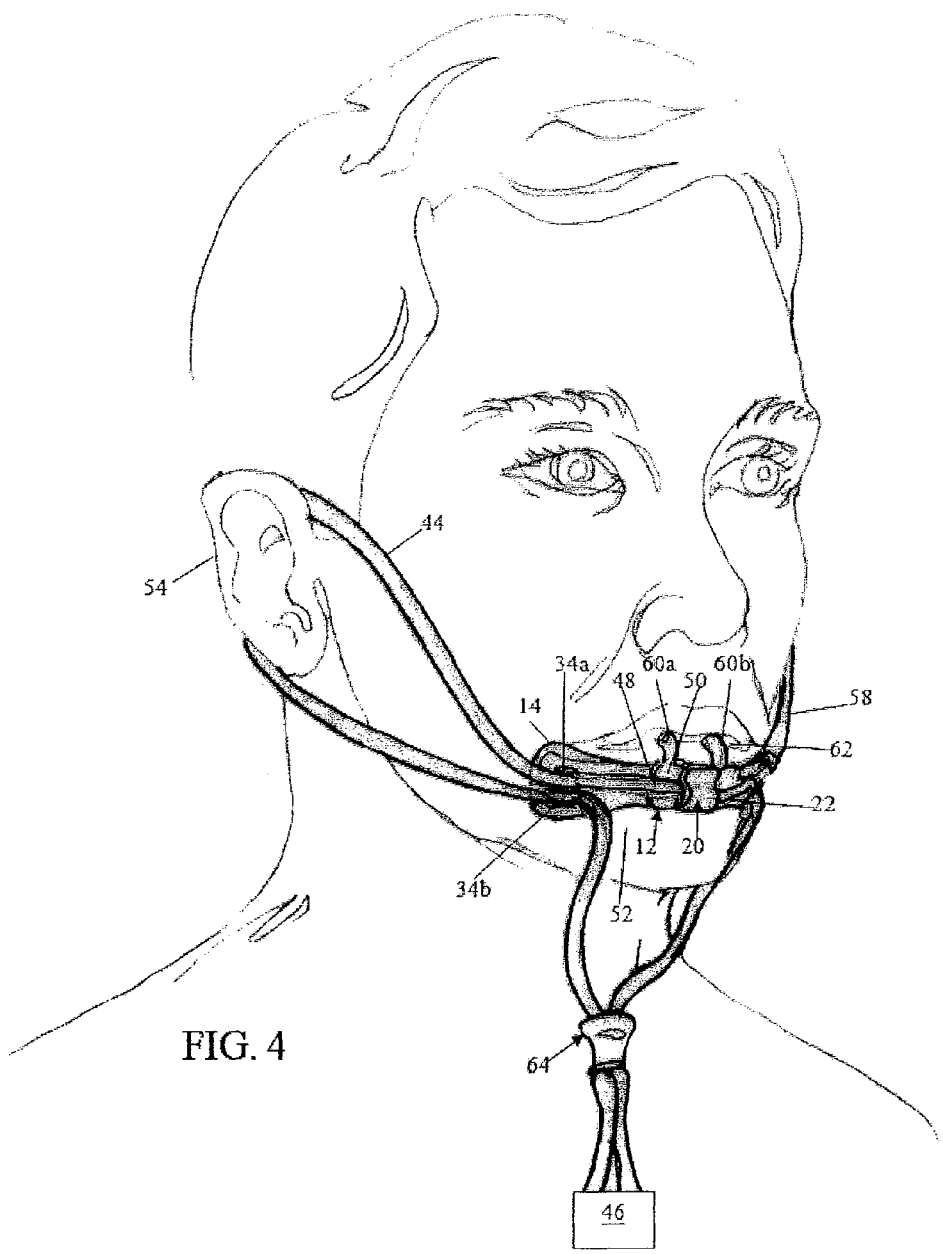
FIG. 4 illustrates the use of the embodiment of the invention shown in FIG. 1 hereof for positioning a nasal cannula for oral administration of gas to a person.

FIG. 4 illustrates the use of the embodiment of the invention shown in FIG. 1 hereof for positioning a nasal cannula for oral administration of gas to a person. Flexible plastic tubing, 44, in gaseous communication with gas source, 46, and with plastic open-ended central tube, 48, of nasal cannula, 50, disposed on chin, 52, below the lower lip of the person, is shown encircling earlobe, 54, as loop, 56. Retainers 34*a* and 34*b*, adapted to receive tubing 44, affix tubing 44 to cannula holder 12, to which cannula 50 is affixed, at two locations, forming thereby loop 56. Cylindrical portion 22 of retention device 20 of cannula 50 is shown as being disposed between parallel tips or prongs, 60*a*, and 60*b*, of tube 48. A similar arrangement is made for flexible tubing, 58, on the left side of the head of the person, tubing 58 also being in gaseous communication with gas source 46. Open tips or prongs, 60*a*, and 60*b*, are illustrated as opening into mouth, 62, of the person such that gas may be orally administered thereto. Slide, 64, enclosing lengths of flexible tubing 44 and 58 and pad 14 assist in further stabilizing cannula support 12 on the face of the person.

Figure 5:
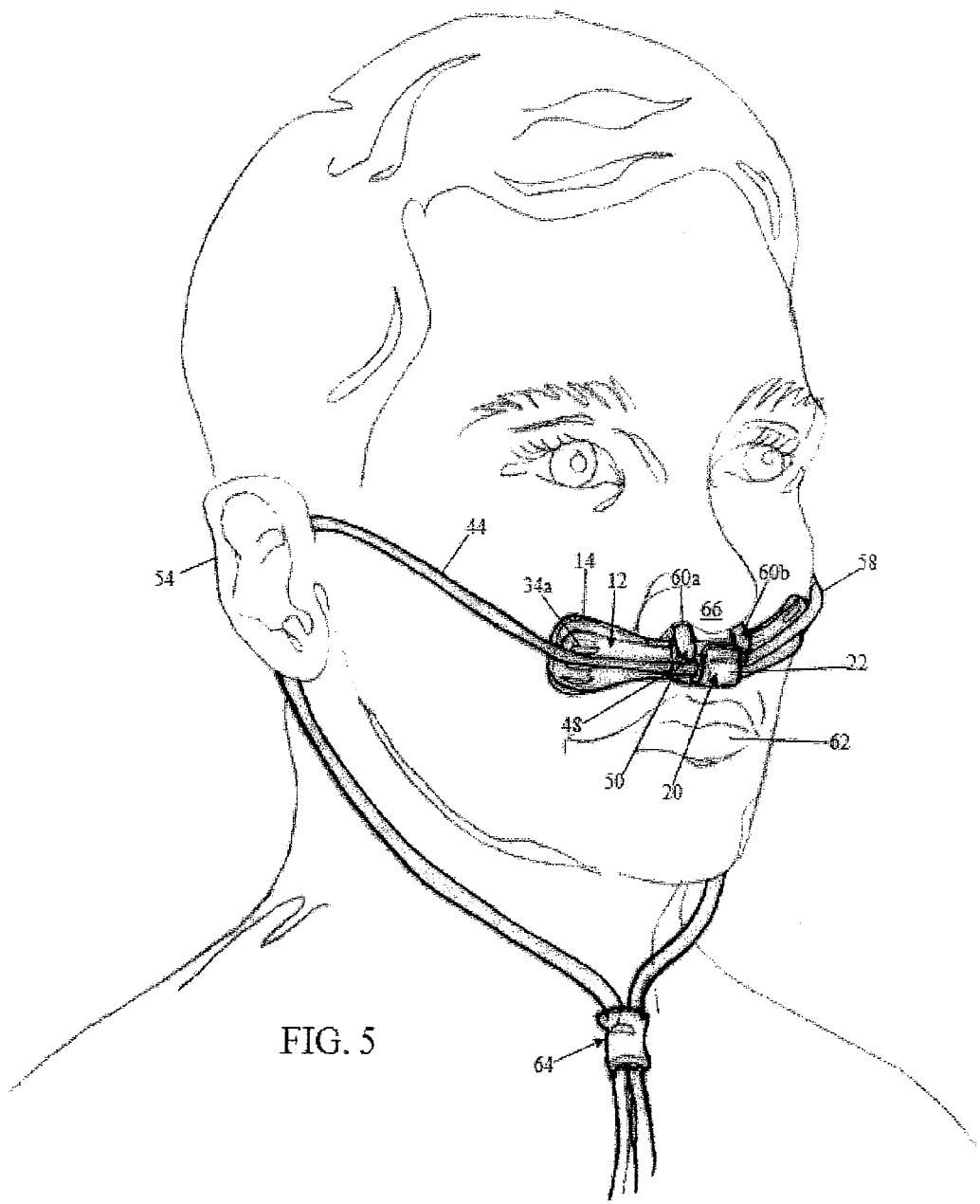
FIG. 5 illustrates the use of the embodiment of the invention shown in FIG. 1 hereof for positioning a nasal cannula for nasal administration of gas to a person.

FIG. 5 illustrates the use of the embodiment of the invention shown in FIG. 1 hereof for positioning a nasal cannula for nasal administration of gas to a person. In this situation, flexible tubes 44 and 58 are affixed to cannula support 12 in one location, illustrated on the right side of the person as in retainer 34*a*. Tips or prongs, 60*a*, and 60*b*, are illustrated as opening into nose, 66, of the person such that gas may be nasally administered thereto. The nares of nose 66 holding prongs 60*a* and 60*b*, the earlobes of the person, pad 14, and slide 64 together provide the stabilization of cannula support 12 on the face of the person.

It should be mentioned that cannula holder 12 may be rotated 180° such that the opening of retention device 20 faces downward in FIG. 5. A similar configuration is also suitable for FIG. 4 hereof. Further, only one of the retainers 30*a* or 30*b*, or 34*a* or 34*b* on either side of cannula 12 need be used to fasten the lengths of flexible tubing on either side of to cannula holder 12 for oral administration of gas, in the same manner as shown in FIG. 5 for nasal administration of gas to a person. That is, each flexible tube may pass along the neck and under the chin of the wearer after leaving the lobe portion of its corresponding ear before entering slide 64 for both types of gas administration.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for positioning a nasal cannula on the face of a person for oral or nasal administration of gas, comprising:
    a flexible cannula support member having a first end and an opposing second end;
    at least one retention device for securing said nasal cannula to said support member;
    a pad that, when said apparatus is worn, is disposed between said support member and the face of said person; and
    a flexible strip having shape memory disposed between said pad and said support member for permitting said support member and said pad to be conformed to the face of said person;
    whereby, said cannula is adapted to be held at a chosen location on the face of said person.

2. The apparatus of claim 1, wherein said support member is generally rectangular in shape.

3. The apparatus of claim 1, wherein said nasal cannula has a first length and a second length of flexible, open-ended tubing, said apparatus further comprising at least one first interference-fit retainer in the vicinity of the first end of said support member for securing said first length of flexible tubing on at least one location thereof to said support member, such that said first length of flexible tubing forms a loop effective for encircling one earlobe of the person; and a least one second raised open channels in the vicinity of the second, opposing end of said support member for securing said second length of flexible tubing on at least one location thereof to said support member, such that said second length of flexible tubing forms a loop effective for encircling the second earlobe of the person.

4. The apparatus of claim 3, further comprising two first interference-fit retainers for securing said first length of flexible tubing at two locations to said support member, and two second interference-fit retainers for securing said second length of flexible tubing at two locations to said support member.

5. The apparatus of claim 1, wherein a portion of said retention device is adapted to fit between two, spaced-apart parallel tubular nostril portions of said cannula.

6. The apparatus of claim 1, wherein said pad is comprises fabric.

7. The apparatus of claim 6, wherein said fabric is hypoallergenic.

8. The apparatus of claim 1, wherein said support member is injection molded.

9. The apparatus of claim 8, wherein said at least one retention device is integrally molded with said support member.

10. The apparatus of claim 1, wherein said pad is affixed to said support member.

11. The apparatus of claim 10, wherein said pad is affixed to said support member using a double-sided, pressure-sensitive adhesive strip.

12. The apparatus of claim 1, wherein said flexible strip comprises aluminum.

13. The apparatus of claim 1, wherein said pad has shape memory to permit said support member and said pad to be conformed to the face of said person.

14. A system for oral or nasal administration of gas to a person, comprising:
    a nasal cannula;
    a flexible cannula support member having a first end and an opposing second end;
    at least one retention device for securing said nasal cannula to said support member;
    a pad that, when said system is worn, is disposed between said support member and the face of said person; and a flexible strip having shape memory disposed between said pad and said support member for permitting said support member to be conformed to the face of said person;

whereby, said cannula is adapted to be held at a chosen location on the face of said person.

15. The system of claim 14, wherein said cannula support member is generally rectangular in shape.

16. The system of claim 14, wherein said cannula has a first and a second length of flexible, open-ended tubing, said system further comprising at least one first interference-fit retainer in the vicinity of the first end of said support member for securing said first length of flexible tubing on at least one location thereof to said support member, such that said first length of flexible tubing forms a loop effective for encircling one earlobe of the person; and a least one second raised open channels in the vicinity of the second, opposing end of said support member for securing said second length of flexible tubing on at least one location thereof to said support member, such that said second length of flexible tubing forms a loop effective for encircling the second earlobe of the person.

17. The system of claim 16, comprising two first interference-fit retainers for securing said first length of flexible tubing at two locations to said support member, and two second interference-fit retainers for securing said second length of flexible tubing at two locations to said support member, wherein said nasal cannula is used for oral administration of gas.

18. The system of claim 14, wherein a portion of said retention device is adapted to fit between two, spaced-apart tubular nostril portions of said cannula.

19. The system of claim 14, wherein said pad is comprises fabric.

20. The system of claim 19, wherein said fabric is hypoallergenic.

21. The system of claim 14, wherein said support member is injection molded.

22. The system of claim 21, wherein said at least one retention device is integrally molded with said support member.

23. The system of claim 14, wherein said pad is affixed to said support member.

24. The system of claim 23, wherein said pad is affixed to said support member using a double-sided, pressure-sensitive adhesive strip.

25. The system of claim 14, wherein said flexible strip comprises aluminum.

26. The system of claim 14, wherein said pad has shape memory to permit said support member and said pad to be conformed to the face of said person.

* * * * *